(12) United States Patent
Dellimore et al.

(10) Patent No.: US 11,931,134 B2
(45) Date of Patent: Mar. 19, 2024

(54) DEVICE, SYSTEM AND METHOD FOR DETECTION OF PULSE OF A SUBJECT

(71) Applicant: KONINKLIJKE PHILIPS N.V., Eindhoven (NL)

(72) Inventors: Kiran Hamilton J. Dellimore, Ut (NL); Mukul Julius Rocque, Eindhoven (NL); Ralph Wilhelm Christianus Gemma Rosa Wijshoff, Munstergeleen (NL); Jens Muehlsteff, Aachen (DE)

(73) Assignee: Koninklijke Philips N.V., The Netherlands (AG)

( * ) Notice: Subject to any disclaimer, the term of this patent is extended or adjusted under 35 U.S.C. 154(b) by 474 days.

(21) Appl. No.: 17/260,845

(22) PCT Filed: Jul. 23, 2019

(86) PCT No.: PCT/EP2019/069848
§ 371 (c)(1),
(2) Date: Jan. 15, 2021

(87) PCT Pub. No.: WO2020/020915
PCT Pub. Date: Jan. 30, 2020

(65) Prior Publication Data
US 2021/0259567 A1 Aug. 26, 2021

Related U.S. Application Data

(60) Provisional application No. 62/703,546, filed on Jul. 26, 2018.

(51) Int. Cl.
*A61B 5/024* (2006.01)
*A61B 5/00* (2006.01)
(Continued)

(52) U.S. Cl.
CPC ........ *A61B 5/02427* (2013.01); *A61B 5/1128* (2013.01); *A61B 5/7207* (2013.01); *G06T 7/246* (2017.01); *G06T 2207/30076* (2013.01)

(58) Field of Classification Search
None
See application file for complete search history.

(56) References Cited

U.S. PATENT DOCUMENTS

| 8,649,562 B2 | 2/2014 | De Haan |
| 2009/0043210 A1 | 2/2009 | Kitoh |
(Continued)

FOREIGN PATENT DOCUMENTS

| JP | 2017086322 A | 5/2017 |
| WO | 2013132850 A1 | 11/2010 |
(Continued)

OTHER PUBLICATIONS

Birkholz et al "Detection of Prehospital Cardiac Arrest by Lays:Validation of a Miniaturized Sensor System in Patients With Cardiopulmonary Bypass"; Abstract, Resuscitation 2011, 8251, S1-S34, p. 59.
(Continued)

*Primary Examiner* — Yi-Shan Yang

(57) ABSTRACT

The present invention relates to a device, system and method for improved non-invasive and objective detection of pulse of a subject. The device comprises an input unit (2a) configured to obtain a series of images of a skin region of the subject and a processing unit (2b) for processing said series of images by detecting pulse-related motion of the skin within the skin region from the series of images, generating a motion map of the skin region from the detected pulse-related motion, comparing the generated motion map with an expected motion map of the skin region, and determining the presence of pulse within the skin region based on the comparison.

13 Claims, 9 Drawing Sheets

(51) Int. Cl.
*A61B 5/11* (2006.01)
*G06T 7/246* (2017.01)

(56) References Cited

U.S. PATENT DOCUMENTS

| | | | | |
|---|---|---|---|---|
| 2010/0172567 | A1* | 7/2010 | Prokoski | A61B 5/0064 |
| | | | | 348/47 |
| 2011/0164035 | A1* | 7/2011 | Liao | A61B 6/487 |
| | | | | 345/419 |
| 2016/0250490 | A1* | 9/2016 | Hoffman | A61N 1/37252 |
| | | | | 607/60 |
| 2017/0277138 | A1* | 9/2017 | Kaji | A61B 5/112 |
| 2018/0053392 | A1 | 2/2018 | White | |
| 2018/0082432 | A1 | 3/2018 | Ishikawa et al. | |
| 2018/0110442 | A1 | 4/2018 | Zalevsky | |
| 2018/0110443 | A1 | 4/2018 | Zalevsky et al. | |
| 2018/0317779 | A1* | 11/2018 | Gregg | A61B 5/1127 |
| 2020/0121262 | A1 | 4/2020 | De Haan | |

FOREIGN PATENT DOCUMENTS

| | | |
|---|---|---|
| WO | 2013136231 A1 | 9/2013 |
| WO | 2015095760 A1 | 6/2015 |
| WO | 20116207306 A1 | 12/2016 |
| WO | 2017191324 A1 | 11/2017 |

OTHER PUBLICATIONS

Bossaert et al: "European Resuscitation Council Guidelines for Resuscitation 2015, Section 11. The Ethics of Resuscitation and End-of-Life Decisions", Resuscitation 95, 2015, pp. 302-311.

Brearley et al: "Peripheral Pulse Palpation:An Unreliable Physical Sign"; Annals of the Royal College of Surgeons of England(1992) vol. 74, pp. 169-171.

Chen et al: "Video Stabilization for Fast Moving Camera Based on Feature Point Classification"; 2015 Third International Conference on Robot, Vision and Signal Processing, pp. 10-13.

Deakin et al: "Accuracy of the Advanced Trauma Life Support Guidelines for Predicting Systolic Blood Pressure Using Carotid for Predicting Systolic Blood Pressure Using Carotid, Femoral, and Radial Pulses:Observational Study"; BMJ, vol. 321, Sep. 2000, pp. 673-674.

Eberle et al: "Checking the Carotid Pulse Check::Diagnostic Accuracy of First Responders in Patients With and Without a Pulse"; Resuscitation 33 (1996), pp. 107-116.

Graham et al: "Evaluation of a New Method for the Carotid Pulse Check in Cardiopulmonary Resuscitation"; Resuscitation 53, (2002), pp. 37-40.

Jaeger et al: "First-Aid Sensor System: New Methods for Single-Point Detection and Analysis of Vital Parameters Such as Pulse and Respiration"; Proceedings of The29th Annual International Conference of the IEEE EMBS, Aug. 2007, pp. 2928-2931.

Lundin et al: "Distal Pulse Palpation:Is It Reliable": World J. Surg, 23, pp. 252-255, 1999.

Moco et al: "Camera-Based Assessment of Arterial Stiffness and Wave Reflection Parameters From Neck Micro-Motion"; IOP Publishing, Physical Measurement, vol. 38 (2017) pp. 1576-1593.

Monsieurs et al: "European Resuscitation Council Guidelines for Resuscitation 2015, Section 1. Executive Summary"; Resuscitation 95 (2015)pp. 1-80.

Moule: "Checking the Carotid Pulse:Diagnostic Accuracy in Students of the Healthcare Professions"; Resuscitation 44 (2000), pp. 195-201.

Ochoa et al: "Competence of Health Professionals to Check the Carotid Pulse"; Resuscitation 37 (1998), pp. 173-175.

PCT/EP2019/069848 ISR & WO, Oct. 11, 2019, 14 Page Document.

Perkins et al: "European Resuscitation Council Guidelines for Resuscitation 2015, Section 2. Adult Basic Life Support and Automated External Defibrillation"; Resuscitation 95 (2015), pp. 81-99.

Soar et al: "European Resuscitation Council Guidelines for Resuscitation 2015, Section 3. Adult Advanced Life Support"; Resuscitation 95 (2015) pp. 100-147.

Tibballs et al: "Reliability of Pulse Palpation by Healthcare Personnel to Diagnose Paediatric Cardiac Arrest"; Resuscitation 80 (2009), pp. 61-64.

Verkruysse et al: "Remote Plethysmographic Imaging Using Ambient Light"; Opt Express, 2008, vol. 16(26), pp. 21434-21445.

* cited by examiner

DEVICE, SYSTEM AND METHOD FOR DETECTION OF PULSE OF A SUBJECT

CROSS-REFERENCE TO PRIOR APPLICATIONS

This application is the U.S. National Phase application under 35 U.S.C. § 371 of International Application No. PCT/EP2019/069848, filed on Jul. 23, 2019, which claims the benefit of U.S. Provisional Patent Application No. 62/703,546, filed on Jul. 26, 2018. These applications are hereby incorporated by reference herein.

FIELD OF THE INVENTION

The present invention relates to a device, system and method for detection of pulse of a subject.

BACKGROUND OF THE INVENTION

Manual palpation is still the gold standard for assessment of pulse presence during cardiopulmonary resuscitation (CPR) for professional and lay rescuers. However, a major challenge in manual palpation is that pulse detection takes too long (often 25 s or more). Palpation requires chest compressions to be interrupted and is performed at the end of a 2-min cycle in the CPR protocol. A lengthy, futile palpation can therefore lead to a long, unnecessary interruption in CPR, which is bad for CPR outcome. Furthermore, palpation is very unreliable as well as highly subjective, with a reported sensitivity of 90% and specificity of 55%. Nevertheless, pulse detection is still perceived by the resuscitation community as a very important technique for the assessment of the need for CPR in an emergency situation and is recommended for Advanced Life Support (ALS) rescuers.

The carotid location is a prominent site for palpation to assess the presence and the strength of a patient's pulse, because of its central location, its large diameter and its ease of access. According to Basic Life Support guidelines, pulse presence measured at the carotid artery refers to systolic blood pressure (SBP) of at least 60 mmHg, whereas at the femoral artery or radial artery a pulse can be palpated at higher pressure levels 70 or 80 mmHg, respectively.

In manual palpation major challenges include:
Manual pulse detection requires interruption of chest compressions and takes too long (often 25 s or more).
Manual palpation is very unreliable as well as highly subjective, with a reported sensitivity of 90% and specificity of 55%.
No convenient method for pulse detection is available, still a very important technique for the assessment of the need to start or to continue CPR in an emergency situation for instance pulse detection via an invasive arterial blood pressure measurement or end-tidal CO2, but this requires either placement of catheters or intubation.
There is a need for a simple, low-cost and reliable sensor that can assist lay rescuers to rapidly identify a cardiac arrest situation requiring CPR (i.e., by recognition that a victim is not breathing and has no pulse) and which can help them determine when CPR should be stopped (i.e., when return of spontaneous circulation or ROSC has occurred).

Hence, there is a need for a device, system and method for non-invasive and objective detection of pulse presence and optionally breathing, particularly for emergency situations.

SUMMARY OF THE INVENTION

It is an object of the present invention to provide a device, system and method for improved non-invasive and objective detection of pulse of a subject.

In a first aspect of the present invention a device for detection of pulse of a subject is presented comprising an input unit configured to obtain a series of images of a skin region of the subject, and a processing unit for processing said series of images by
detecting pulse-related motion of the skin within the skin region from the series of images,
generating a motion map of the skin region from the detected pulse-related motion,
comparing the generated motion map with an expected motion map of the skin region, and
determining the presence of pulse within the skin region based on the comparison.

In a further aspect of the present invention a system for detection of pulse of a subject is presented comprising
an imaging unit configured to acquire a series of images of a skin region of the subject, and
a device for detection of pulse of a subject as disclosed herein based on the acquired series of images.

In yet further aspects of the present invention, there are provided a causing a computer to perform the steps of the method disclosed herein when said computer program is carried out on a computer as well as a non-transitory computer-readable recording medium that stores therein a computer program product, which, when executed by a processor, causes the method disclosed herein to be performed.

Preferred embodiments of the invention are defined in the dependent claims. It shall be understood that the claimed method, system, computer program and medium have similar and/or identical preferred embodiments as the claimed device, in particular as defined in the dependent claims and as disclosed herein.

The present invention is based on the idea to evaluate a series of images, e.g. video images taken by a camera, from a skin region of the subject's skin, e.g. from the carotid location, which is accepted and recommended by the medical community as a standard location for pulse assessment. Pulse-related motion of the skin within the skin region, e.g. carotid pulsations, as derived from the series of images, is used to generate a motion map of the skin region, e.g. showing the strength of motion in the different areas of the skin region. This motion map is then compared to an expected motion map of the skin region, e.g. showing the expected strength of motion in the different areas of the skin region for a subject showing "normal" pulse-related motion of the skin, for instance from a healthy subject having a heart beat in a normal frequency and amplitude range. From this comparison it can be determined if pulsation within the skin region is present or not, i.e. this comparison provides an indication of return of spontaneous circulation (i.e., ROSC) in CPR. This information may then guide e.g. a rescuer to continue with CPR or not.

The present invention overcomes the aforementioned current problems in assessment of pulse presence during cardio-pulmonary resuscitation as well as offers a general tool for basic health checks in the continuum of care. The presented device and method can be used for on-body and off-body non-invasive, objective and reliable detection of pulse presence and optionally breathing for emergency situations, but can be used in low acuity or personal healthcare applications as well. Use of the invention enables a quick and robust assessment of pulse presence within the recommended pulse check time window of <10 s.

In an embodiment the processing unit is further configured to derive a dilatation signal reflecting arterial dilatation from the generated motion map and to compare the derived dilatation signal with an expected dilatation signal related to the expected motion map for comparing the generated motion map with the expected motion map of the skin particularly at the carotid location due to the prominent visibility of the arterial dilatation. From this arterial dilatation a dilatation signal can be obtained, which can be compared to an expected dilatation signal related to the expected motion map to get pulse-related information, e.g. if ROSC is present or not.

The dilatation signal comes from dilation and contraction of the carotid artery due to the pumping of blood by the heart. Arterial dilatation causes "skin doming" when a part of the skin surface directly above the artery moves up and down relative to the surrounding skin. The dilatation may be detected in the images by the motion signal, e.g. in combination with a detected arterial/venous network.

Preferably, the processing unit is further configured to detect frequency and/or amplitude of the derived dilatation signal and to compare the detected frequency and/or amplitude with an expected frequency and/or amplitude and/or with a frequency and/or amplitude threshold or range (e.g. using upper and lower thresholds for frequency and/or amplitude). This provides an efficient way of obtaining the desired pulse-related information.

The processing unit may further be configured to detect a pulse movement region within the series of images for use as a skin region. Generally, the images may not necessarily show only the desired skin region, but may show a complete scene. For instance, a camera may monitor a complete patient sitting or lying in bed or a mobile camera may show the complete upper body or the complete head and neck of a patient. Hence, using e.g. image processing means may be used to find a good skin region, e.g. the carotid location, from pulse movements detected in the images. Such image processing means may use generally known motion detection algorithms to detect movements of the skin caused by the pulsating blood.

For this purpose, the processing unit may further be configured to detect landmarks within the series of images and to detect the pulse movement region based on the detected landmarks.

Such landmarks may be detected from vascular network information of the subject, which reflects the vascular network of the subject. Such vascular network information may be obtained from said series of images or separate image information of the subject, in particular near-infrared images of the skin region of the subject. Hence, if the images contain information in the near-infrared (NIR) spectral region, this information can be evaluated to derive the vascular network information. Alternatively, a separate NIR camera may be used to obtain such NIR image information used to derive the vascular network information. Landmarks in the vascular network information may be characteristic branches and junctions in the arterial and/or venous vascular network.

The use of the vascular network information further overcomes problems of handheld camera-based devices in terms of motion robustness by taking into account the vascular network as a reference grid in order to correct for relative motions of camera and signal sources. Further, body landmarks and/or the vascular network information may be used for the detection of physiologically motivated expected body locations of pulse signal and/or respiration signal presence.

Such landmarks may further be used in an embodiment to perform motion compensation of the series of images for compensating (non-pulsatile originated) motion of the subject's body not related to pulse of the subject. Thus, undesired motion, e.g. caused by movements of the subject and/or changes of the lighting and/or chest compression during CPR, can be identified and compensated to stabilize the motion map and to avoid negative influences on the evaluation of the pulse-related motion in the skin region. Hence, the need for disruptive pauses in chest compression may thereby be eliminated.

The processing unit may further be configured to generate a photo-plethysmographic, PPG, signal from the series of images, derive a pulse signal from the PPG signal, and determine the presence of pulse within the skin region based on the comparison and the pulse signal. The additional use of the PPG signal, which may be derived from the same images using the well-known technique of remote PPG (as e.g. described in Verkruijsse et al., "*Remote plethysmographic imaging using ambient light*", Optics Express, 16(26), 22 Dec. 2008, pp. 21434-21445), further improves the reliability of the detection of pulse of the subject, in particular of ROSC. Further, a signal fusion of artery dilatation signals may be made in synchronicity with observed superficial blood volume changes (as represented by the PPG signal) for use in the detection of pulse.

In an embodiment the processing unit is further configured to check the pulse signal and the dilatation signal for coincidence of pulse presence, in particular for a time difference between pulses in the pulse signal and the dilatation signal. If the time difference is too large (i.e. above a time difference threshold in the range of 25-100 ms, e.g. of 25 ms in one application or even of 100 ms in another application), this may be used as an indication that at least one of the pulse signal and the dilatation signal may not be caused by pulsation but by other motion or may represent an artifact.

In still another embodiment the processing unit may further be configured to indicate a pulse having an amplitude above a first amplitude threshold and a frequency above a first frequency threshold, in particular an amplitude above a first amplitude threshold and below a second amplitude threshold and a frequency above a first frequency threshold and below a second frequency threshold. For instance, if the amplitude of the dilatation signal is large (e.g. in a range of 1-2 mm) this is indicative of pulse presence and strong pulse strength, and therefore presence of ROSC is assumed. In contrast, a low dilatation amplitude (e.g. in a range of less than 0.5 mm) is indicative of a weak pulse and low pulse strength, and therefore absence of ROSC is assumed. Generally, the amplitude should be in the range of 0.5-2.0 mm to indicate that pulsation is present.

The processing unit may further be configured to generate guiding information from a series of images for guiding an imaging unit for acquiring the series of images or a user operating the imaging unit to the pulse movement region and to generate a control signal controlling the imaging unit to switch from a remote mode, in which first images of the skin region are acquired from a distance, to a contact mode, in which second images of the skin region are acquired with the imaging unit being in contact with or at a distance below e.g. 1 cm (other (smaller or larger) thresholds could be used as well) from the skin for the skin region, wherein the second images are used for determining the presence of pulse. This provides the advantage that in contact mode the presence of skin-related pulse may generally be determined with higher reliability than in remote mode.

The images are preferably obtained by a camera and represent reflective (ambient and/or dedicated illumination) light or colored light having a frequency corresponding to an absorption frequency of blood.

The processing unit may further be configured to determine respiratory motion based on the comparison. Hence, besides pulse detection, the proposed solution may also detect respiration activity simultaneously (i.e., the breathing check which is recommended by current resuscitation guidelines), which is another key vital sign and difficult to assess in real life. For this detection, skin movements with a periodicity of the typical respiration rate (i.e., in the range of 12-18 breaths per minute for adults, up to 40 breaths per minute for children) may be observed for this purpose.

In another embodiment the processing unit may be configured to assess the motion map for detection of artery dilatation present in an expected body area versus another body area in which no motion is expected. This can further improve the detection of pulse by confirming that the motion detected in the expected body area is pulse related and not an Generally, separate devices for basic life checks are hardly available. The presented device and method can be implemented in a conventional, often available user device, such as a smartphone, smart watch or tablet, e.g. as an app, or in wearing glasses such as Google Glass. Alternatively, it can be realized as a standalone device for basic life checks e.g. in first aid kits or in professional clinical settings. Such a device can be used by medical professionals, fire fighters, police men, in mass casualty situations for quick and reliable check, and for military use.

BRIEF DESCRIPTION OF THE DRAWINGS

These and other aspects of the invention will be apparent from and elucidated with reference to the embodiment(s) described hereinafter. In the following drawings

DETAILED DESCRIPTION OF THE INVENTION

Figure 1:
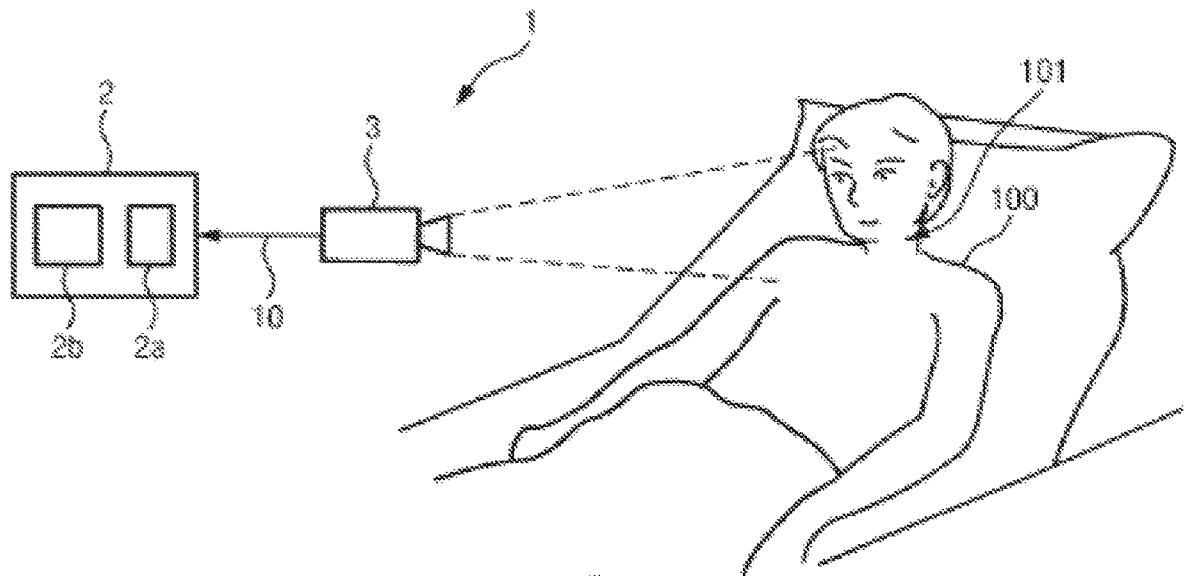
FIG. 1 shows a schematic diagram of a first embodiment of a system and a device according to the present invention.

FIG. 1 shows a schematic diagram of a first embodiment of a system 1 and a device 2 according to the present invention. The system 1 for detection of pulse of a subject 100 comprises an imaging unit 3, e.g. a camera, configured to acquire a series of images 10 of a skin region 101 of the subject. The subject 100 may e.g. be an emergency patient who is treated by CPR or a patient in a hospital or an elderly care home. The skin region 101 may be region of the skin or neck, preferably the carotid location where pulse can be well observed. The images may depict a larger scene not only including skin, which may require further image processing to identify a desired skin region.

The system 1 further comprises a device 2 for detection of pulse of the subject 100 based on the acquired series of images. The device 2 generally comprises an input unit 2a (e.g. a data interface) configured to obtain (i.e. receive or retrieve) a series of images 10 of a skin region of the subject from the camera 3, either via a wired or wireless connection, and a processing unit 2b (e.g. a processor) for processing said series of images 10. The device 2 may e.g. be implemented in software and/or hardware, e.g. as a correspondingly programmed processor or computer. It may be a separate device or part of a conventional user device, such as a smartphone, smart watch, tablet, picture camera, glasses, etc.

Figure 2:
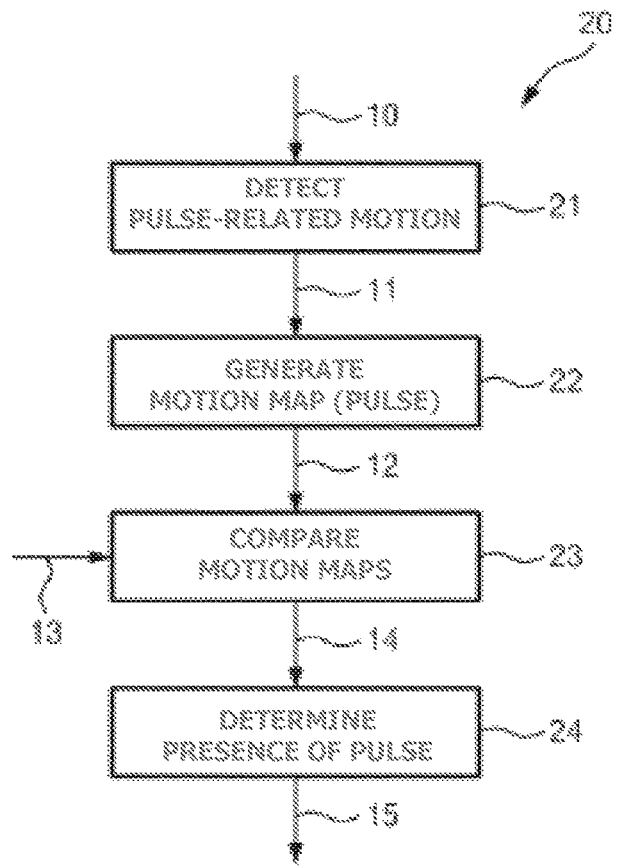
FIG. 2 shows a flow chart of a first embodiment of a method according to the present invention.

FIG. 2 shows a flow chart of a first embodiment of a method 20 according to the present invention. In a first step 21 pulse-related motion 11 of the skin within the skin region is detected from the series of images 10. In a second step 22 a motion map 12 of the skin region 101 is generated from the detected pulse-related motion 11. In a third step 23 the generated motion map 12 is compared with an expected motion map 13 of the skin region, which may e.g. be stored in a storage unit. In a fourth step 24 the presence of pulse is determined within the skin region based on the comparison, i.e. the result 14 of the comparison is used to generate an indication 15 if pulse is present within the subject 100 or not.

The expected motion map 13 preferably represents pulse-related skin motion of a healthy person. Hereby, different expected motion maps may be available for different kinds of patients, e.g. for different ages, different genders, different health status, etc.

In an embodiment, step 23 of comparing the generated motion map 12 with an expected motion map 13 of the skin region comprises a step of deriving a dilatation signal reflecting arterial dilatation from the generated motion map and a step of comparing the derived dilatation signal with an expected dilatation signal related to the expected motion derived compared with an expected frequency and/or amplitude. Alternatively or in addition, the frequency and/or amplitude of the derived dilatation signal may be compared with a frequency and/or amplitude threshold or range. For instance, in the case of a male adult patient, the typical range of pulse rate and amplitude of pulse of a healthy male adult person may be used for this comparison.

Figure 3:
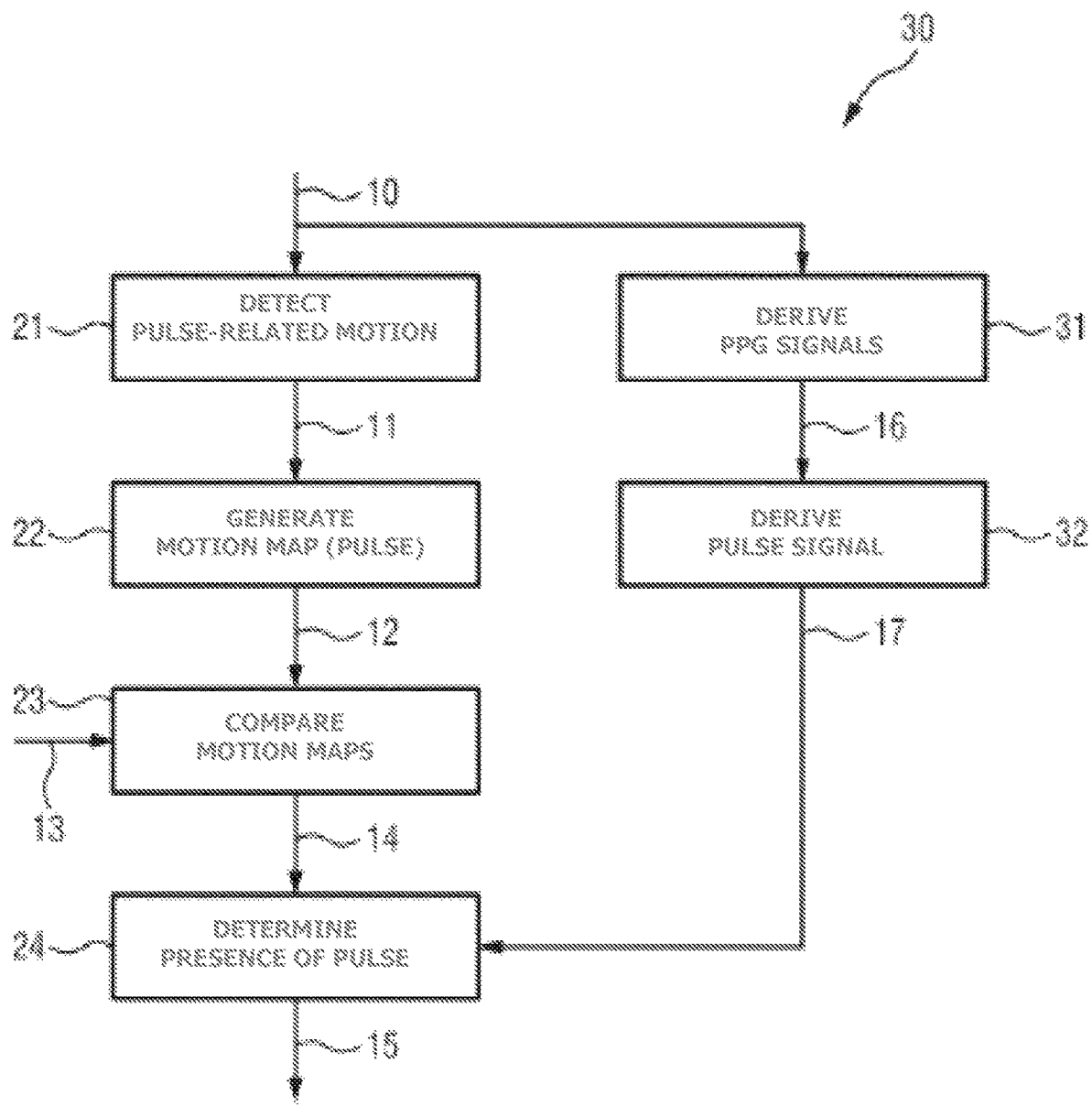
FIG. 3 shows a flow chart of a second embodiment of a method according to the present invention.

FIG. 3 shows a flow chart of a second embodiment of a method 30 according to the present invention. In this embodiment, a second signal is derived from the images and used for independently deriving a pulse signal used in the determination of pulse. In particular, in step 31 a PPG signal 16 is derived from the series of images 10, which is then used to derive a pulse signal 17 from the PPG signal 16 in step 32. This pulse signal 17 is then used in addition to the result 14 of the comparison in step 23 to determine the presence of pulse within the skin region in step 24.

In a practical realization of this embodiment, remote monitoring of pulse from a distance with a static or handheld camera is exploited. Video processing of data acquired by the camera generates robust motion maps from the area of interest (e.g. head and carotid location) and deduces pulse presence from i) color changes of the skin (using remote PPG technique) and ii) presence of a dilatation signal from the carotid. As result, an indication (signal 15) of a life sustaining pulse is provided if both signal sources indicate pulse presence and the detected pulse has a sufficiently high and stable rate. Hereby, various modifications and implementations, e.g. as needed for a particular application or as appropriate for a particular type of patient, may be made. Further, in an implementation the existence of pulse in only one of the two signal sources may be considered sufficient to determine that pulse is present, e.g. if the other signal source is unreliable or not existent at all. Further, in an implementation the device may be configured to take appropriate action, e.g. to issue an alarm or guide the user to change a setting of the camera (e.g. the viewing direction, the distance from the patient, the sensitivity, etc.) if no signal or only the dilatation signal is present.

Figure 4:
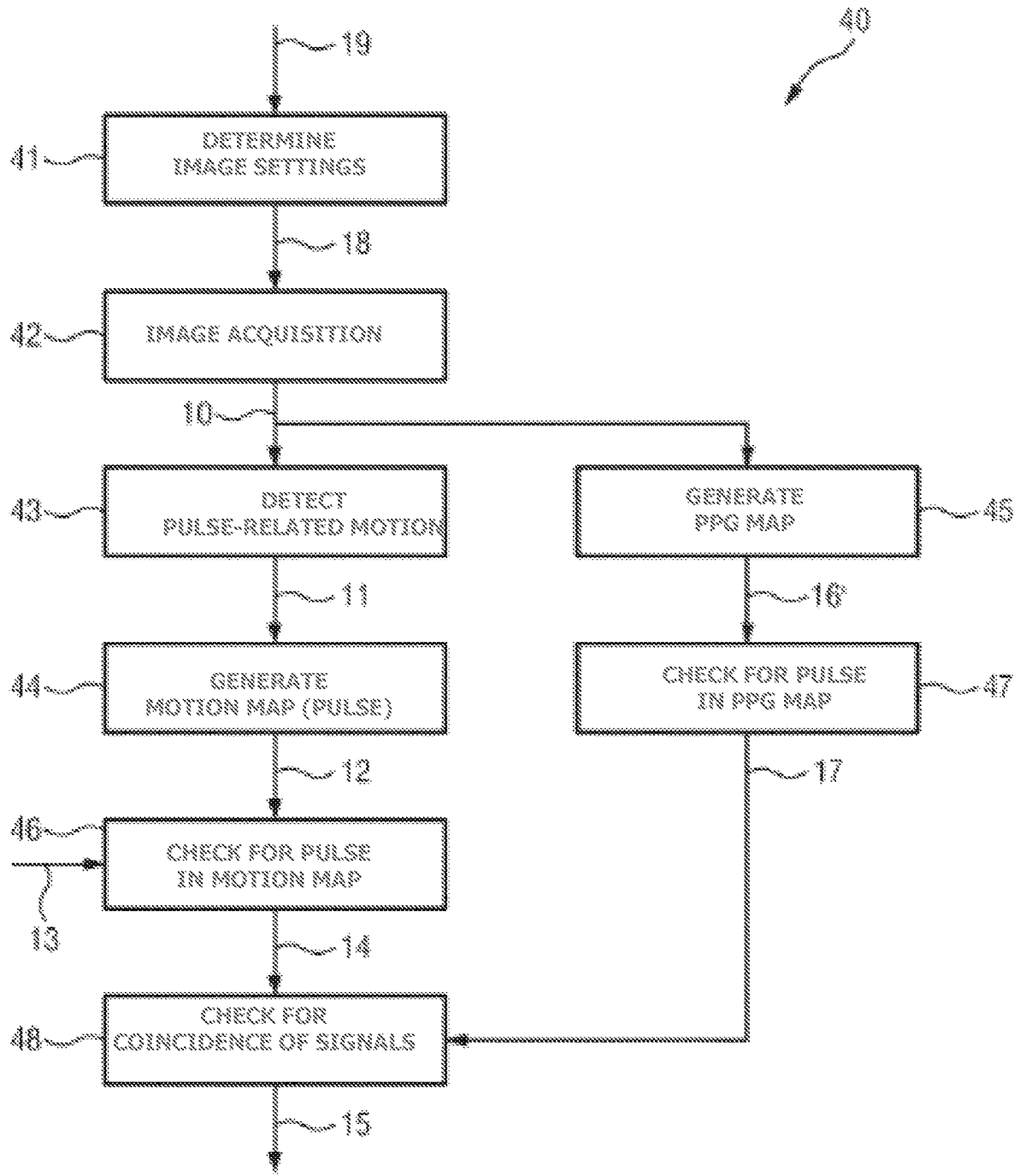
FIG. 4 shows a flow chart of a third embodiment of a method according to the present invention.

FIG. 4 shows a flow chart of a third embodiment of a method 40 according to the present invention. In this embodiment, in an initial step 41 (or repeatedly or continuously during the operation) optimal image acquisition settings, such as optimal magnification and viewing direction, are determined and used to control the camera (via a control signal 18) for subsequent acquisition or during current acquisition of images 10 in step 42. For instance, a vascular (arterial and/or venous) network, represented by vascular network information 19, information may be acquired in advance or during the image acquisition by a near-infrared (NIR) camera or the same camera as used for image acquisition and may e.g. be stored in a storage unit. The venous network of a hand is shown as an example in FIG. 5.

Further, in step 41 a pulse movement region for use as skin region, such as the carotid location, may be detected from the vascular network information 19. For instance, landmarks may be used, e.g. derived from the vascular network, such as characteristic branches and/or junctions.

As an alternative, the pulse movement region may be detected initially in step 43 (substantially corresponding to step 21) based on the series of images 10. Within the images 10 landmarks may be detected and used to detect the pulse movement region.

Body landmarks and, if available, vascular network (e.g. made visible as reference) may further be used for compensation of relative motion artefacts in step 22 or 23 in order to stabilize the motion map and remove motion that is not caused by the beating heart as much as possible, such a motion caused by movements of the body initiated by the subject or resulting from CPR chest compression. Further, other image artefacts as e.g. caused by changing lighting conditions may be observed and compensated as well.

In step 44 (substantially corresponding to step 22) a real-time stabilized motion (i.e., skin pulsation) in the form of a motion map 12 is computed and in step 45 (substantially corresponding to step 31) a PPG map 16' is computed based on body landmarks and, optionally, venous/arterial trees by appropriate imaging techniques (e.g. NIR).

Subsequently a combined analysis of the stabilized motion map 12 and the PPG map 16' is performed. The presence of artefacts may be checked so that they can be corrected, before the stabilized motion map 12 and the PPG map 16' are used to derived pulse-related signals.

In step 46 (substantially corresponding to step 23) pulse is checked in the motion (i.e., skin pulsation) map 12. For instance, it is checked for pulse presences at expected skin area for an artery dilation signal including plausibility checks in expected signal decrease with increasing distance from carotid location. If the contrast is appropriate, pulse presence is deduced from the artery dilatation.

In step 47 (substantially corresponding to step 32) pulse is checked in video color information (substantially corresponding to step 32) (i.e. the PPG map 16').

In step 48 it is checked for coincidence of pulse presence in both signals 14 the pulses in both independent pulse signals should be within a certain acceptable range. For instance, in an exemplary embodiment presence of pulse is determined if the pulse signal and the dilatation signal independently indicate a pulse having an amplitude above a first amplitude threshold and a frequency above a first frequency threshold, in particular an amplitude above a first amplitude threshold and below a second amplitude threshold and a frequency above a first frequency threshold and below a second frequency threshold. If pulse presence is only detected in the dilatation signal (i.e. the motion map) a low perfusion pressure may be indicated and it may be recommended to have manual palpation check or to start CPR.

Figure 6A:
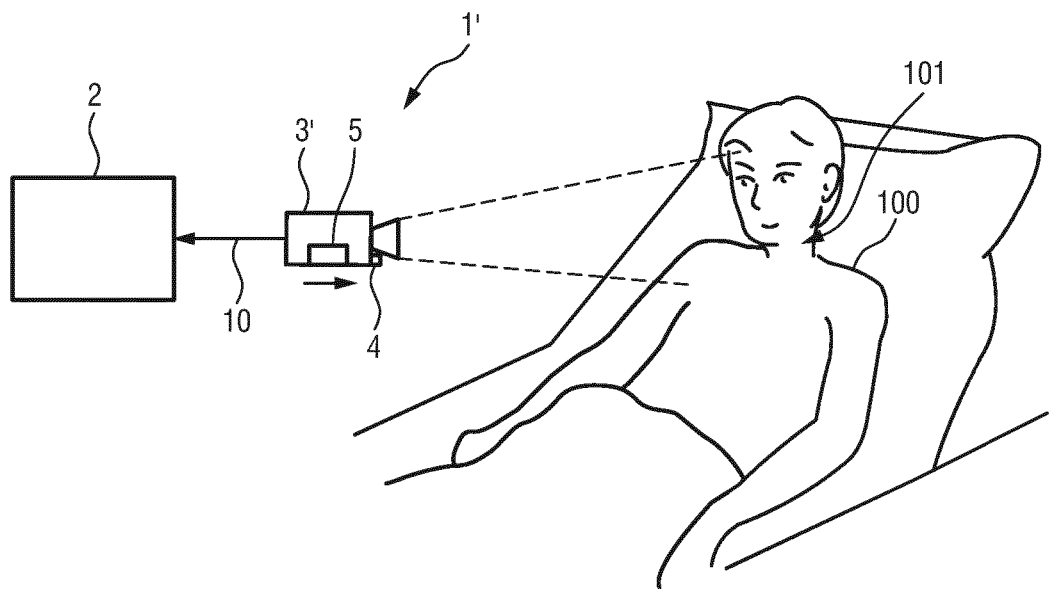
FIG. 6A shows a schematic diagram of a second embodiment of a system according to the present invention in remote mode.
Figure 6B:
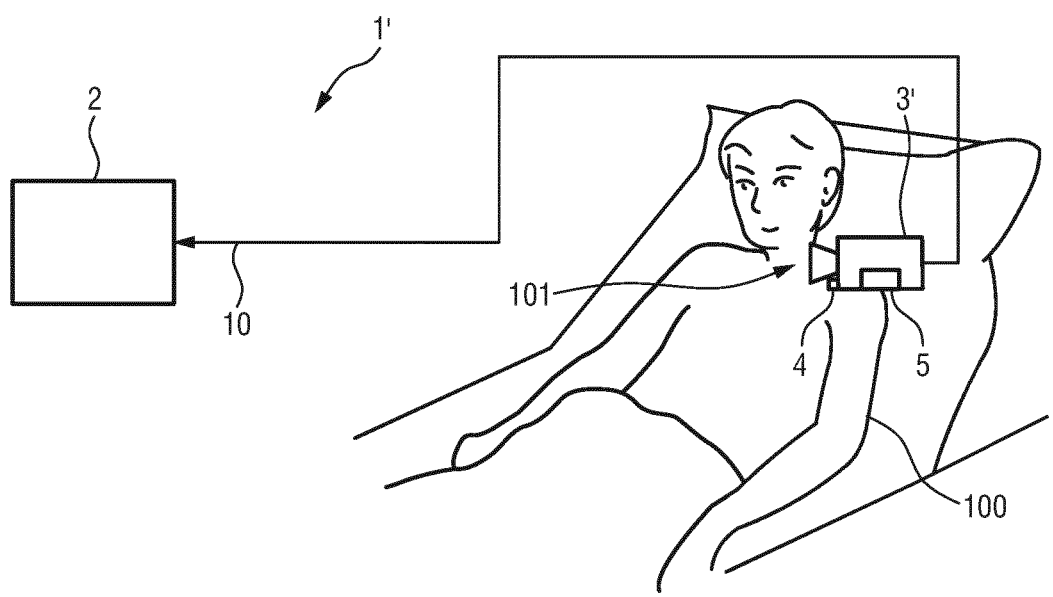
FIG. 6B shows a schematic diagram of the second embodiment of the system according to the present invention in contact mode.
Figure 7:
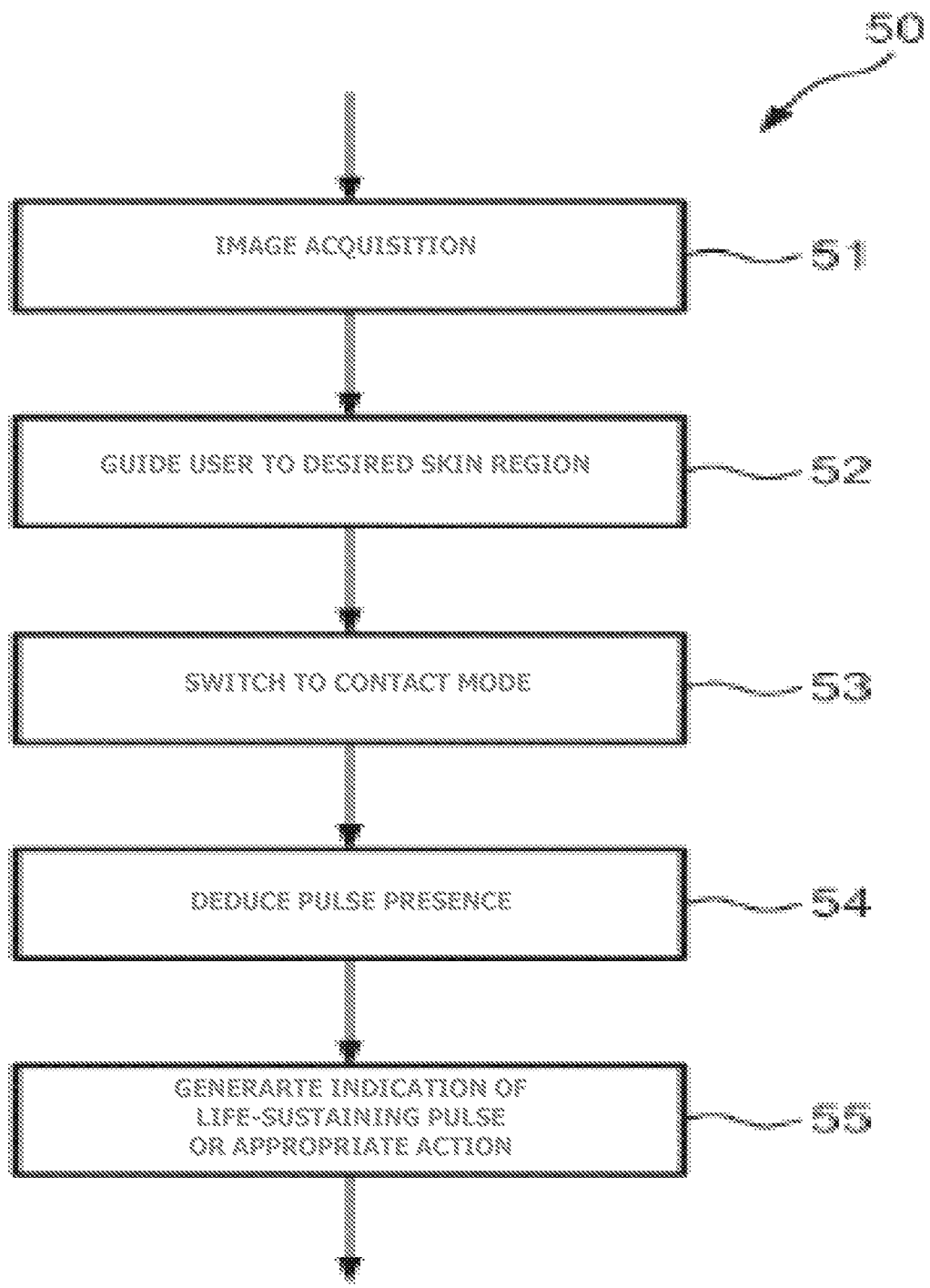
FIG. 7 shows a flow chart of a fourth embodiment of a method according to the present invention.

FIG. 6 shows a schematic diagram of a second embodiment of a system 1' and a device 3' according to the present invention, wherein FIG. 6A shows it in remote mode and FIG. 6B shows it is contact mode. FIG. 7 shows a flow chart of a corresponding embodiment of a method 50 according to the present invention, which may be used by this system 1'. In this embodiment an on-body (contact) vital sign check for assessment in acute care situation is used.

In a first step 51 the images 61 (in particular a video) are continuously acquired in remote mode (shown in FIG. 6A) from a distance using a movable or handheld camera 2. These images 61 are used in step 52 to guide the user (or directly the camera 2) to the desired skin region, e.g. the recommended carotid location. Location information is maintained when the camera 3' is approaching the body and the sensor mode switches to contact mode (shown in FIG. 6B) in step 53, when the camera 3' is close to the skin (e.g. at a distance of 1 cm or less) or touches the skin.

In contact mode, inferred from motion robust maps from the optimal area of interest (e.g. head and carotid location) pulse presence is deduced in step 54 from i) color changes of the skin and ii) presence of a dilatation signal from the carotid. An indication of a life-sustaining pulse is provided in step 55 if both signal sources indicate pulse presence and the detected pulse has a sufficiently high and stable rate. If no signal or only the dilatation signal is present, it is indicated in step 55 to take appropriate action.

In contact mode a dedicated light source 4, e.g. an LED mounted at the camera 3', preferably illuminates the skin region. The light received from the skin in response to said illumination is sensed by the camera and evaluated to obtain the dilatation signal and the PPG signal.

Further, an orientation sensor 5, preferably mounted at the camera, may be Thus, the camera or user can be guided to the optimal placement, e.g. by use of a light spot to mark the carotid location. Further, orientation changes may thus be corrected via signals from the orientation sensor and, optionally, body landmarks.

With this embodiment of the system 1', when approaching the body, the user can be guided to the best recommended location for pulse detection. The video recording is started off-body. The body location and the orientation of the camera may be taken as references and corrected for the changes in the camera position relative to the body when approaching the body, in order to keep physiological constraints for optimal body location.

As in other embodiments, a motion map (i.e. skin pulsation) and a PPG map may be used for pulse presence inference. Further, an automatic adjustment may be provided for optimal magnification, e.g. for the size of the detected arteries/veins. A check is made for coincidence of pulse presence in both signals. If the PPG signal is missing, it may be checked for motion presence including a plausibility check of geometries/physiological constraints. Motion contrast in the motion map may be used to deduce motion presence in plausible body area. Further, a check for pulsatility versus artifact may be made. If only motion is present, a low perfusion pressure may be indicated and/or it may be recommended to have manual palpation check or start CPR.

The camera may also be used to perform an assessment of environmental conditions, hazards and terrain challenges. Challenging terrain (e.g., bush, soft snow, sloping, rocky or uneven ground, etc.), harsh environmental conditions (e.g., snow, mist, fog, rain, low lighting) and safety hazards (e.g., downed power lines, fire, smoke, vehicle traffic, etc.) present significant barriers to the delivery of effective CPR, and may partly contribute to the reported low post-CPR survival rate (for out of hospital cardiac arrest) of 9.5-11.4%. For example, performing chest compressions during CPR on an inclined or soft back support surface will produce shallower, less effective compressions, which will lead to poorer survival outcomes. Moreover, current CPR guidelines recommend that prior to initiation of CPR lay rescuers should always check for any potential hazards and should only approach the victim after determining that the scene is safe. This is especially important since many people may act impulsively and place themselves in harm's way, due to difficulties in thinking clearly as a result of the highly stressful emergency situation.

Figure 5:
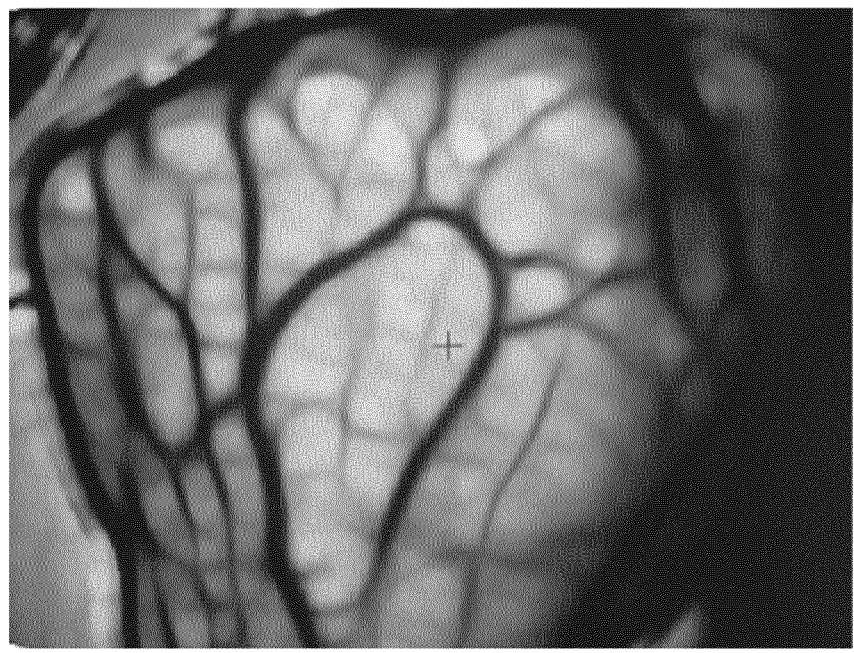
FIG. 5 shows an NIR image of the venous network of a hand.

In practical applications there is a high possibility of relative motion between the camera and the subject. In such cases, the output video from the camera should be stabilized so that the only motion now left is due to heart beat, e.g. the pulsating carotid. This contrast like hair etc., but in low contrast areas such as the region around the carotid stabilization can be challenging with conventional RGB cameras. One way to improve stabilization or registration of frames can be using the underlying venous network to provide the necessary distinctive features. FIG. 5 shows an example of the increase of contrast and distinctive features when the skin is viewed in near-infrared.

Figure 8:
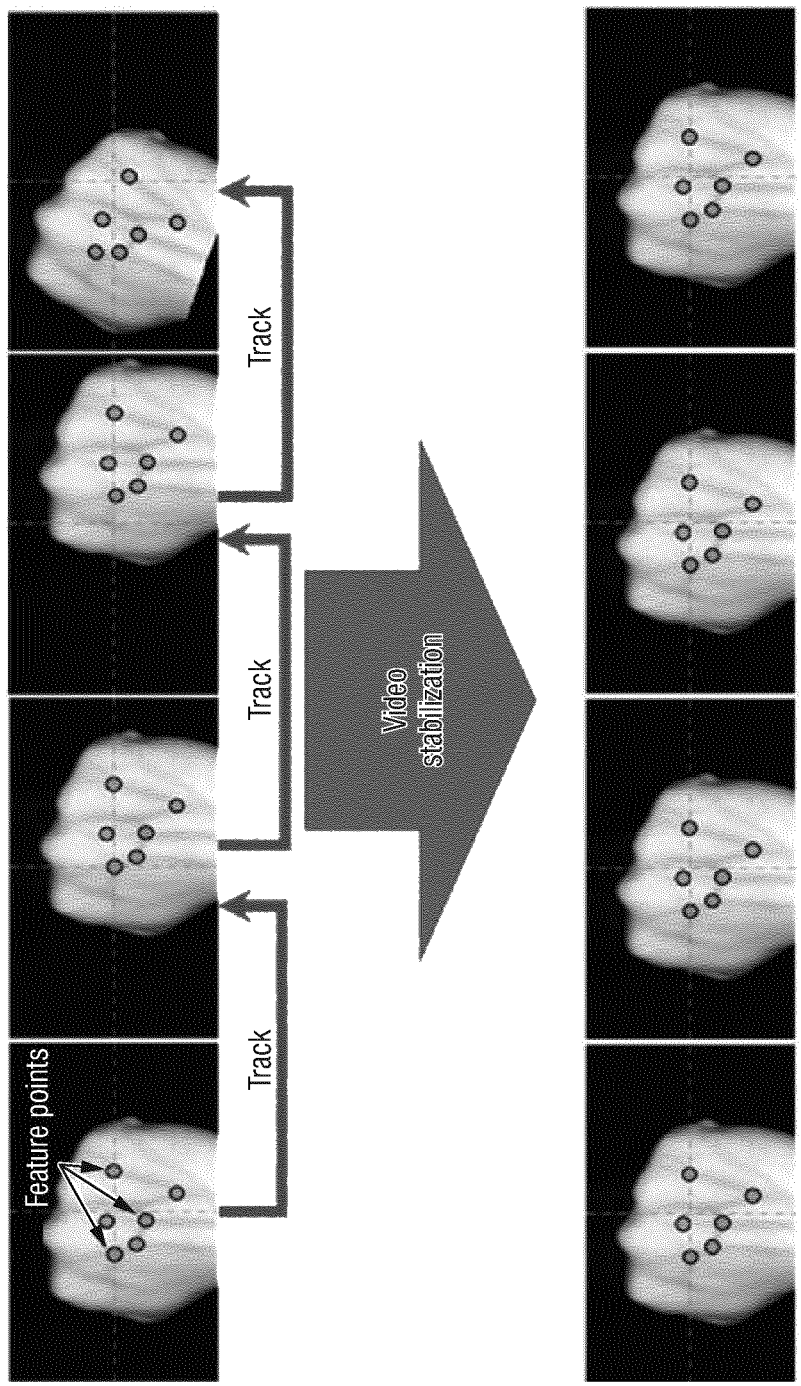
FIG. 8 illustrates video stabilization based on feature point tracking in NIR images of skin.

With such a distinctive set of features the video stabilization can be made very robust. An example of this approach is illustrated in FIG. 8. Here the infrared image of the hand is shown along with the detection of the distinct feature points (high contrast regions such as corners). In each frame these features are detected and then the image is transformed such that the features lie on top of each other in subsequent frames. This leads to a stabilized video where the relative motion between the camera and the subject is minimized greatly if not completely removed. Once stabilized the infrared video stream can also be used to measure the carotid motion.

Figure 9:
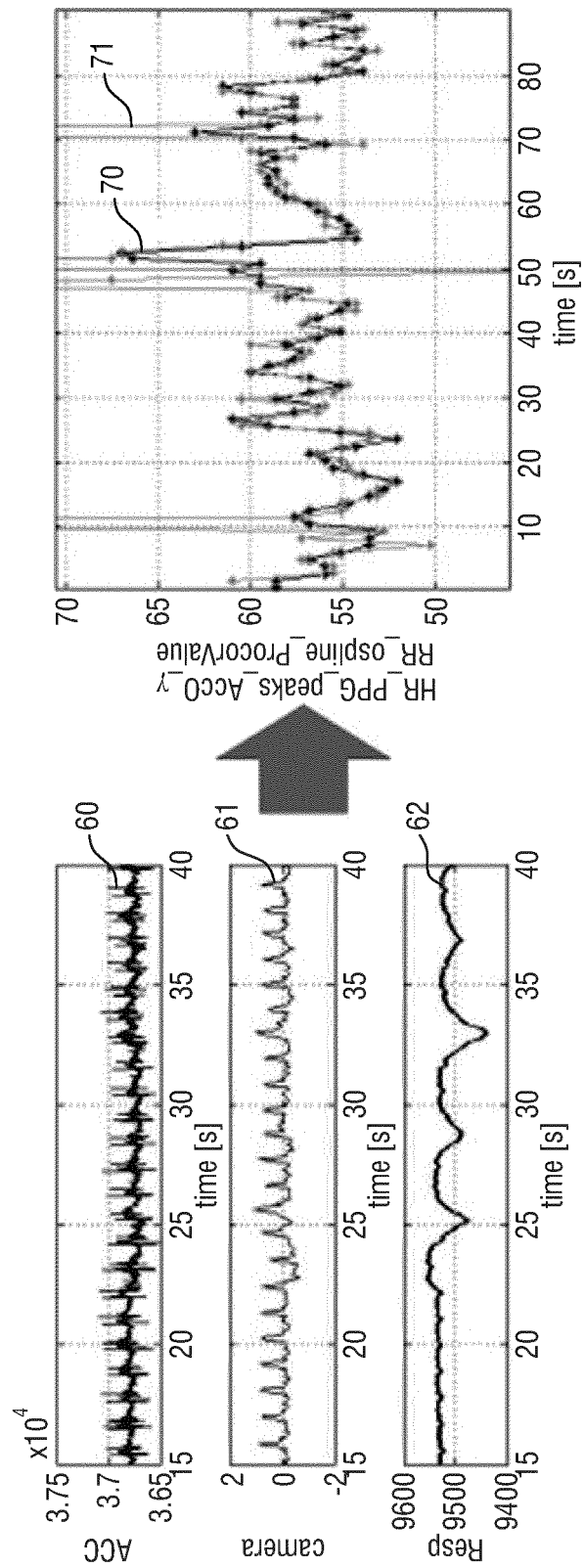
FIG. 9A shows exemplary measurement signals including an accelerometer signal, a pulse signal obtained from skin motion and a respiration signal.
FIG. 9B shows a comparison of a heart rate inference from reference sensor and a camera signal.

FIG. 9A shows exemplary measurement signals including an accelerometer signal 60, a pulse signal 61 obtained from skin motion and a respiration signal 62 and FIG. 9B shows a comparison of a heart rate inference 70 from reference sensor and a camera signal 71. Obviously there is a good overlap. It shall be noted that absolute heart rate accuracy is of less importance for CPR applications.

Figure 10:
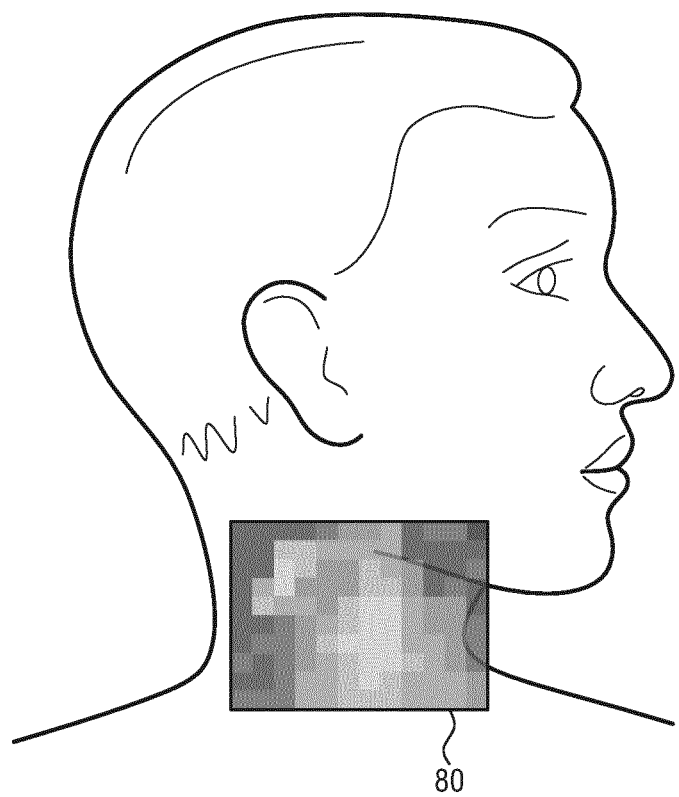
FIG. 10 shows an exemplary motion map of the carotid location.

FIG. 10 shows an exemplary motion map 80 of the carotid location. The grey zones mark areas with high motion signal due to carotid dilation. Obviously, observed motion is largest in an area, where the carotid is located underneath. The motion signal strength decreases when moving outwards away from the carotid artery, which is expected as well. In combination with a detected arterial/venous network, the obtained dilatation signal can be more accurately and reliably evaluated even when there is no signal present.

The present invention can be applied in advanced cardiopulmonary resuscitation (CPR), e.g. for in-hospital CPR (e.g. to monitor defibrillators) or out-of-hospital CPR by medical professionals (e.g. advanced AEDs having PPG and a cuff-based blood pressure measurement on board). Further applications are in basic life support and lay responders (e.g. AEDs for public use, with PPG and cuff-based blood pressure measurements on board), mass casualty triaging, combat casualty assessment in military settings, and home monitoring solutions where people can sit in front of a (web-)camera to measure their pulse and breathing rate. The disclosed device may be implemented in smartphones, smartwatches tablets or as standalone device.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

A computer program may be stored/distributed on a suitable non-transitory medium, such as an optical storage medium or a solid-state medium supplied together with or as part of other hardware, but may also be distributed in other forms, such as via the Internet or other wired or wireless telecommunication systems.

Any reference signs in the claims should not be construed as limiting the scope.

The invention claimed is:

1. A device for detection of a pulse of a subject associated with a cardiopulmonary resuscitation of the subject, the device comprising:
   an input unit configured to obtain a series of images of a skin region of the subject associated with the cardiopulmonary resuscitation of the subject; and
   a processing unit for processing said series of images, the processing unit being configured to:
   detect pulse-related motion of a skin within the skin region of the subject from the series of images;
   generate a motion map of the skin region of the subject from the detected pulse-related motion;
   derive a dilatation signal reflecting arterial dilatation from the generated motion map;
   compare the derived dilatation signal with an expected dilatation signal related to an expected motion map of a skin region for a healthy subject;

determine and indicate a presence of a pulse within the skin region of the subject associated with the cardiopulmonary resuscitation of the subject based on the comparison; and at least one of:

generate guiding information from a second series of images for guiding an imaging unit for acquiring the series of images or guiding a user for operating the imaging unit to the pulse movement region; and generate a control signal controlling the imaging unit to switch from a remote mode, in which first images of the skin region are acquired from a distance, to a contact mode, in which second images of the skin region are acquired with the imaging unit being in contact with or in proximity of the skin for the skin region, wherein the second images are used for determining the presence of the pulse.

2. The device as claimed in claim 1, wherein the processing unit is further configured to:

detect frequency and/or amplitude of the derived dilatation signal; and compare the detected frequency and/or amplitude with an expected frequency and/or amplitude and/or with a frequency and/or amplitude threshold or range.

3. The device as claimed in claim 1, wherein the processing unit is further configured to detect a pulse movement region within the series of images for use as the skin region of the subject.

4. The device as claimed in claim 3, wherein the processing unit is further configured to:

detect landmarks within the series of images; and detect the pulse movement region based on the detected landmarks.

5. The device as claimed in claim 4, wherein the processing unit is further configured to detect the landmarks from vascular network information of the subject.

6. The device as claimed in claim 5, wherein the processing unit is further configured to generate the vascular network information from said series of images or separate image information of the subject.

7. The device as claimed in claim 1, wherein the processing unit is further configured to:

detect landmarks within the series of images; and perform motion compensation of the series of images for compensating motion of the subject's body not related to the pulse of the subject.

8. The device as claimed in claim 1, wherein the processing unit is further configured to:

derive a photo-plethysmographic, PPG, signal from the series of images;

derive a pulse signal from the PPG signal; and determine the presence of the pulse within the skin region based on the comparison and the pulse signal.

9. The device as claimed in claim 1, wherein the processing unit is further configured to check the pulse signal and the derived dilatation signal for coincidence of pulse presence.

10. The device as claimed in claim 9, wherein the processing unit is further configured to determine the presence of pulse if the pulse signal and the dilatation signal independently indicate a pulse having an amplitude above a first amplitude threshold and a frequency above a first frequency threshold.

11. A system for detection of a pulse of a subject during a cardiopulmonary resuscitation of the subject, the system comprising:

the device for detection of the pulse of the subject as claimed in claim 1 based on the series of images; and an imaging unit configured to acquire the series of images of the skin region of the subject during the cardiopulmonary resuscitation of the subject.

12. A method for detection of a pulse of a subject associated with a cardiopulmonary resuscitation of the subject, the method comprising:

obtaining a series of images of a skin region of the subject associated with the cardiopulmonary resuscitation of the subject; and processing said series of images including:

detecting pulse-related motion of the skin within the skin region from the series of images;

generating a motion map of the skin region from the detected pulse-related motion;

deriving a dilatation signal reflecting arterial dilatation from the generated motion map;

comparing the derived dilatation signal with an expected dilatation signal related to an expected motion map of a skin region for a healthy subject;

determining a presence of a pulse within the skin region associated with the cardiopulmonary resuscitation of the subject based on the comparison; and at least one of:

generate guiding information from a second series of images for guiding an imaging unit for acquiring the series of images or guiding a user for operating the imaging unit to the pulse movement region; and generate a control signal controlling the imaging unit to switch from a remote mode, in which first images of the skin region are acquired from a distance, to a contact mode, in which second images of the skin region are acquired with the imaging unit being in contact with or in proximity of the skin for the skin region, wherein the second images are used for determining the presence of the pulse.

13. A non-transitory computer-readable recording medium comprising program code means for causing a computer to carry out the steps of the method as claimed in claim 12 when said steps of the method as claimed in claim 12 is carried out on the computer.

* * * * *